(12) United States Patent
Morton

(10) Patent No.: US 8,570,030 B2
(45) Date of Patent: Oct. 29, 2013

(54) MAGNETIC SENSOR FOR DETERMINING WEAR

(75) Inventor: Scott A. Morton, Laramie, WY (US)

(73) Assignee: University of Wyoming, Laramie, WY (US)

( * ) Notice: Subject to any disclaimer, the term of this patent is extended or adjusted under 35 U.S.C. 154(b) by 246 days.

(21) Appl. No.: 13/131,848

(22) PCT Filed: Nov. 30, 2009

(86) PCT No.: PCT/US2009/066119
§ 371 (c)(1),
(2), (4) Date: May 27, 2011

(87) PCT Pub. No.: WO2010/063028
PCT Pub. Date: Jun. 3, 2010

(65) Prior Publication Data
US 2011/0227565 A1   Sep. 22, 2011

Related U.S. Application Data

(60) Provisional application No. 61/118,652, filed on Nov. 30, 2008.

(51) Int. Cl.
*G01B 7/14* (2006.01)
*G01N 27/72* (2006.01)

(52) U.S. Cl.
USPC ........ 324/207.2; 324/251; 324/225; 324/228; 324/240

(58) Field of Classification Search
USPC ....................... 324/207.2, 251, 225, 228, 240
See application file for complete search history.

(56) References Cited

U.S. PATENT DOCUMENTS

| | | | |
|---|---|---|---|
| 2,548,599 A | 4/1951 | Garr | |
| 3,440,527 A | 4/1969 | Steingroever | |
| 4,229,696 A | 10/1980 | Gustafson | |
| 5,583,426 A | 12/1996 | Tiefnig | |
| 6,060,880 A | 5/2000 | Guyot et al. | |
| 2001/0055183 A1 | 12/2001 | Cain et al. | |
| 2006/0219528 A1 | 10/2006 | Aizawa et al. | |
| 2008/0042860 A1 | 2/2008 | Gai et al. | |
| 2008/0179813 A1 | 7/2008 | Sells et al. | |

FOREIGN PATENT DOCUMENTS

DE   102005016346 B3   1/2007

OTHER PUBLICATIONS

International Search Report for PCT/US2009/066119, International Searching Authority, Jan. 29, 2010, pp. 1-9.

*Primary Examiner* — Reena Aurora
(74) *Attorney, Agent, or Firm* — Samuel M. Freund; Cochran Freund & Young LLC

(57) ABSTRACT

An apparatus and method for detecting wear of a surface of an object or part, and directing the measured amount of wear to an interface such that an operator may be apprised of this value are described. One end of the sacrificial wear sensor hereof is disposed such that it experiences the same wear as the surface of the part to be monitored. One embodiment of the present sensing element includes a permanent magnet fixedly sandwiched between two plates having high magnetic permeability material, wherein magnetic poles are oriented perpendicular to the plates. The plates extend beyond the magnet on the side thereof opposite the wear edge, forming thereby an air gap such that magnetic flux is concentrated in the plates with the magnetic circuit being completed through the air gap between the plate extensions. A magnetic flux monitoring device may be disposed in the air gap of the sensing element for measuring the magnetic flux density in the gap. As the magnet and the plates of the sensing element are worn away by the same mechanism that causes wear on the part being monitored, the magnet volume decreases, thereby decreasing the flux density in the air gap. This decrease in flux density can be related to the wear of the surface under investigation.

33 Claims, 7 Drawing Sheets

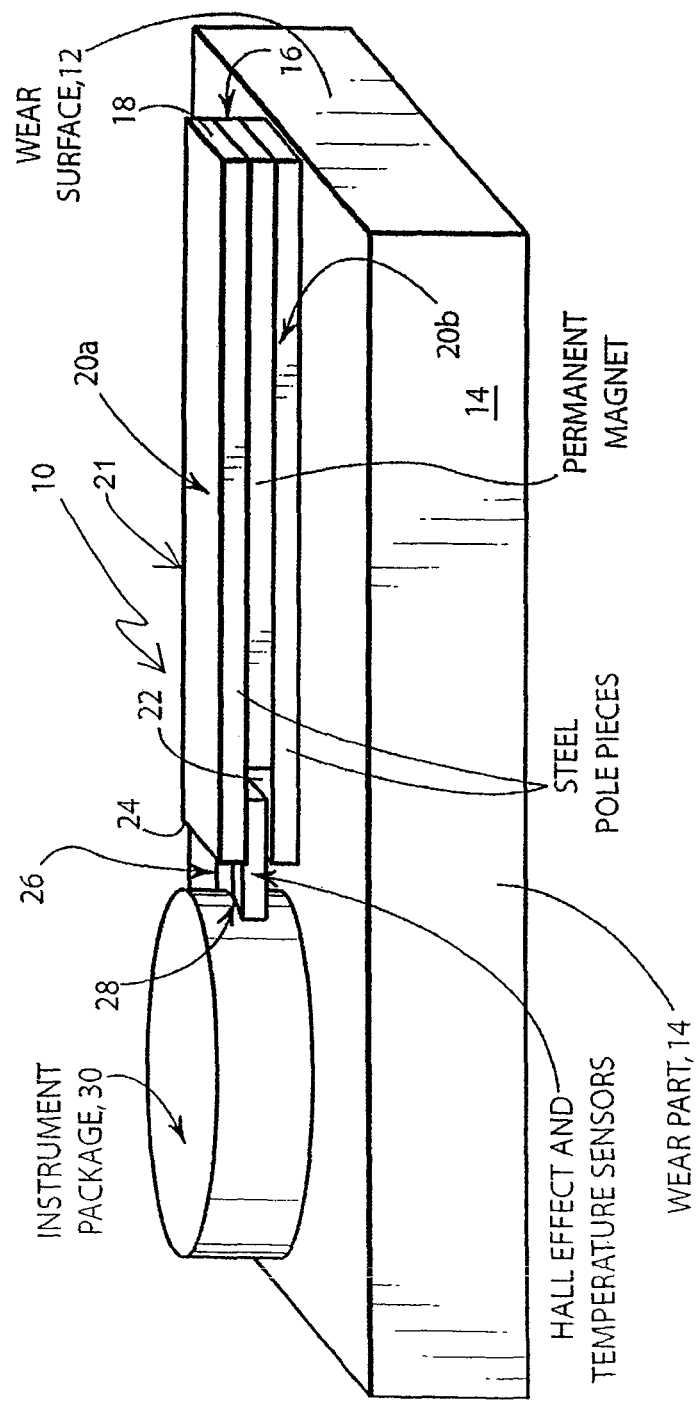

MAGNETIC SENSOR FOR DETERMINING WEAR

RELATED CASES

This application is the U.S. National Stage Patent Application of International Application No. PCT/US2009/0066119, filed on Nov. 30, 2009, which claims the benefit of U.S. Provisional Patent Application Ser. No. 61/118,652 for "Magnetic Sensor for Determining Wear" by Scott A. Morton, filed on Nov. 30, 2008, which applications are hereby incorporated by reference herein for all that they disclose and teach.

FIELD OF THE INVENTION

The present invention relates generally to the measurement of wear of materials and, more particularly, to the use of a sacrificial magnetic sensor for measuring the amount of wear of the materials.

BACKGROUND OF THE INVENTION

Various equipment and devices such as snow plows, agricultural tillage implements, earth-moving equipment, clutches, and brakes, as examples, have replaceable parts and surfaces that move relative to other parts or substrates and that may significantly wear during the operational life of such parts. If such parts are not replaced before the wear becomes too severe, extensive collateral damage may occur to adjacent parts and structures. Repairing such collateral damage or replacing damaged parts may be expensive and time-consuming. In addition, a wearing part, such as a carbide-edged snowplow blade, may itself be expensive and require significant time to replace. Therefore, premature prophylactic replacement of such parts represents an unnecessary cost in time and materials.

A sensor for measuring a change of a magnetic field including a magnet for generating a constant magnetic flux and magnetically conductive members for producing a first magnetic field passing through an object capable of influencing the first magnetic field, and a second magnetic field which does not pass through the object, and a magnetic field measuring device located in the second magnetic field for measuring changes in the second magnetic field resulting from changes in the first magnetic field, is described in U.S. Pat. No. 4,229,696 for "Sensor For Measuring Magnetic Field Changes" which issued to Adolf G. Gustafson on Oct. 21, 1980.

SUMMARY OF THE INVENTION

Accordingly, it is an object of embodiments of the present invention to provide an apparatus and method for accurately measuring wear of surfaces and edges.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the wear sensor, hereof, includes in combination: an elongated magnet having a first length along the long dimension thereof, a first long flat side and an opposing second, long flat side; a first magnetically permeable material having a second length and a flat side disposed alongside the first flat side of the magnet; a second magnetically permeable material having a third length and a flat side disposed alongside the second flat side of the magnet, wherein the second length and the third length are greater than the first length, forming thereby a closed end and an air gap between the first material and the second material at the opposing end; and means for measuring the magnetic field within the air gap; whereby the magnetic field in the air gap decreases as the magnet, the first material and the second material are worn away at the closed end.

In another aspect of the invention, and in accordance with its objects and purposes, the method for determining wear experienced by an object, hereof, includes the steps of: interposing an elongated magnet having a first length along the long dimension thereof, a first long flat side and an opposing second long flat side between a first magnetically permeable material having a second length and a flat side disposed alongside the first flat side of the magnet, and a second magnetically permeable material having a third length and a flat side disposed alongside the second flat side of the magnet, wherein the second length and the third length are greater than the first length, forming thereby a closed end and an air gap between the first material the second material at the opposing end; exposing the closed end to the same wear as experienced by the object; and measuring the magnetic field within the air gap; whereby the magnetic field in the air gap decreases as the magnet, the first material and the second material are worn away at the closed end.

In yet another aspect of the invention, and in accordance with its objects and purposes, the wear sensor, hereof, includes in combination: an elongated magnet having a first length along the long dimension thereof, a long flat side, and a pole direction parallel to the flat side; a first magnetically permeable material having a second length and a flat side disposed alongside the flat side of the magnet; a second magnetically permeable material having a third length and a flat side disposed alongside the flat side of the magnet, wherein the second length and the third length are less than the first length, wherein the magnet and the first permeable material form a first closed end, wherein the magnet and the second permeable material form an opposing second closed end, and wherein the first permeable material and the second permeable material form an air gap therebetween on the flat side of the magnet; and means for measuring the magnetic field within the air gap; whereby the magnetic field in the air gap decreases as the magnet, and the first permeable material are worn away at the first closed end.

In still another aspect of the invention, and in accordance with its objects and purposes, the wear sensor, hereof, includes in combination: an elongated magnet having a first length along the long dimension thereof, a long flat side, and a pole direction parallel to the first flat side; a magnetically permeable material having a second length and a flat side disposed alongside the flat side of the magnet, wherein the second length is greater than the first length, forming thereby a closed end and an opposing end wherein the magnetically permeable material extends beyond the flat side of the elongated magnet; and means for measuring the magnetic field in the vicinity of the extended permeable material; whereby the magnetic field in vicinity of the extended permeable material decreases as the magnet and the permeable material are worn away at the closed end.

Benefits and advantages of the present invention include, but are not limited to, providing an apparatus and method for measuring wear on surfaces using a magnetic sensor without a requirement that magnetic fields generated by the sensor pass through the surface being monitored, or a requirement that the surface being monitored is magnetically permeable.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings:

FIG. 1 is a schematic representation of a perspective view of an embodiment of the magnetic sensor for determining wear of a surface of an object of the present invention, illustrating an elongated permanent magnet having at least two parallel long sides, magnetically permeable plates between which the magnet is interposed, a probe for measuring the magnetic field in an air gap formed by the plates, and an instrument package for controlling, analyzing and transmitting the measurements, all of which may be mounted on the object for which surface wear is to be monitored.

FIG. 2A is a schematic representation of a side view of the magnetic portion of the magnetic sensor shown in FIG. 1 hereof, illustrating the magnetic flux generated by an elongated permanent magnet having magnetic poles perpendicular to two long parallel sides thereof, and passing principally through an air gap formed by magnetically permeable plates between which the magnet is interposed, at the end thereof opposite to the end of the magnetic portion of the sensor exposed to wear, while

FIG. 3A is a schematic representation of a side view of the magnetic portion of the magnetic sensor shown in FIG. 1 hereof, showing the magnetic flux generated by an elongated permanent magnet having magnetic poles parallel to two long parallel sides thereof, and passing principally through an air gap between magnetically permeable plates between which the magnet is interposed, at the end thereof opposite to the end of the magnetic portion of the sensor exposed to wear, while

FIG. 4A is a schematic representation of a side view of the magnetic portion of the magnetic sensor shown in FIG. 1 hereof, showing the magnetic flux generated by an elongated permanent magnet having magnetic poles parallel to at least one long side thereof, and passing principally through an air gap formed between two spaced apart magnetically permeable plates disposed on the at least one long side of the magnet, whereby the magnet surface is exposed, while

FIG. 5A is a schematic representation of a side view of the magnetic portion of the magnetic sensor shown in FIG. 1 hereof, showing the magnetic flux generated by an elongated permanent magnet having magnetic poles parallel to the at least one side thereof, and passing principally through an air gap formed by an L-shaped magnetically permeable plate having its long dimension adjacent to the at least one long side of the magnet, while

FIG. 6A is a schematic representation of an embodiment of the instrument package shown in FIG. 1 hereof powered by an energy harvesting module, while

DETAILED DESCRIPTION OF THE INVENTION

Figure 2A:
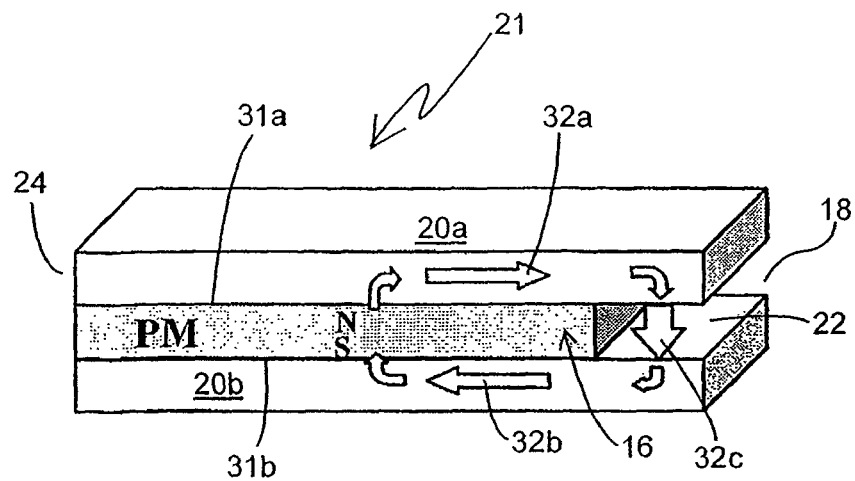

Briefly, the present invention includes an apparatus and method for detecting wear of a surface of an object or part over the entire range of wear of the surface, and transmitting the measured amount of wear to an interface, or otherwise indicating the amount of wear, such that a user of the object may be apprised of this value. Projections of remaining service lifetime for the wearing part may be calculated, and warnings and/or alarms may be provided for imminent end-of-life thereof. One end of the sensor is disposed such that it experiences the same wear as the surface of the part to be monitored. One embodiment of the sacrificial sensing element, hereof, includes an elongated permanent magnet having two parallel long sides fixedly interposed between two magnetically permeable plates, and wherein the magnetic poles are oriented perpendicular to the parallel sides of the magnet. The plates extend beyond the magnet on the side thereof opposite the wear edge, thereby forming an air gap such that magnetic flux is concentrated in the plates with the magnetic circuit being completed through the air gap between the plate extensions. A Hall Effect sensor or probe, or other magnetic flux monitoring device, may be disposed in the air gap of the magnetic sensing element for measuring the magnetic flux density in the gap. As the magnet and the plates of the sensing element are worn away by the same mechanism that causes wear on the part being monitored, the magnet length decreases, thereby decreasing the flux density in the air gap. This decrease in flux density may then be related to the wear of the part.

Another embodiment of the magnetic sensor may include an elongated magnet having poles oriented parallel to at least one long flat side of the magnet. At least one magnetically permeable plate is placed alongside the at least one flat side of the magnet. If two parallel plates having long dimensions larger than the magnet are employed, forming thereby an air gap, the magnetic flux may bifurcate within the air gap and the density may be measured near the surface of one of the plates. However, only one plate may be used and the magnetic field exiting the magnet and entering the plate may be monitored. As the magnet and the plates of the sensing element are worn away by the same mechanism that causes wear on the part being monitored, the magnet length in the direction of the magnetization decreases, thereby decreasing the flux density near the surface of the plates in the air gap.

In another embodiment of the magnetic sensor, the magnetic portion of the sensor may include an elongated magnet having a flat side parallel to the magnetic poles of the magnet, and first and second magnetically permeable plates having lengths, the sum of which is smaller than the length of the magnet, and placed in contact with the flat side of the magnet, whereby an air gap is formed between the plates, and wherein the magnet surface is exposed. With this configuration, the magnetic flux density in the gap between the first and second plates would increase, and the fringe flux would decrease. Again, as the magnet and first plate wear, the magnetic flux in the gap decreases as a function of the amount of wear since the length of the magnet decreases. For such a configuration, the length of wear that can be measured may be reduced because of the reduced usable magnet length, but the sensitivity of measurement may be increased.

In another embodiment of the invention, the magnetic sensor may include an elongated magnet having a flat long side to which the orientation of the magnetic poles is parallel, and an L-shaped magnetically permeable plate having a length such that when the flat side of the magnet is placed along the long side of the "L", an air gap is formed between the plate and the magnet, whereby an end of the magnet is exposed to the plate. The magnetic flux density in the air gap may increase, and the fringe flux may decrease with this configuration. Again, as the magnet and first plate wear, the magnetic flux in the gap decreases as a function of the amount of wear. For such a configuration, the length of wear that can be measured may be reduced, but the sensitivity of measurement may increase.

The apparatus hereof may further include a microprocessor for translating the signals from the Hall Effect sensor into wear terminology, a transceiver for wireless communication with a user interface either remote from or adjacent to the wear sensor, a temperature sensor to compensate for temperature variation of the magnetic flux density, and an energy harvesting device for supplying power for the associated instrumentation. The microprocessor may store calibration values for a plurality of sensors, receiving periodic readings from each sensor, and translate the readings into meaningful information for the operator. The microprocessor may also provide long-term data to facilitate maintenance, procurement and dispatch scheduling. This data may be stored for periodic transfer, or transmitted to support facilities in real time.

Reference will now be made in detail to the present embodiments of the invention, examples of which are illustrated in the accompanying drawings. In the Figures, similar or identical structure will be identified using the same reference characters. Turning now to FIG. 1 a schematic representation of an embodiment of magnetic sensor, 10, for determining the wear of surface, 12, of object, 14, is shown. Elongated permanent magnet, 16, interposed between magnetically permeable plates, 20a and 20b, form magnet portion, 21, with magnet 16 having a wear surface, 18, which is disposed such that it experiences similar wear to the wear experienced by surface 12 of object 14. Plates 20a and 20b may be fabricated from any material having magnetic permeability as long as it is sufficiently ductile to wear under abrasion rather than fracturing. Materials such as steel and soft magnetic composites where iron particles are embedded in an electrically insulating resin are expected to be useful. Suitable magnet materials may include ductile materials which wear instead of fracturing or shattering. Flexible magnetic materials, where magnetic powder is embedded in a rubber matrix or in a more rigid thermoplastic or thermoset plastic material, and where the magnetization is throughout the thickness of the matrix, as an example, are expected to be useful in the practice of the present invention. Flexible magnetic sheets again having magnetization throughout the thickness thereof may also be used. Iron-Chromium-Cobalt magnets may be employed if they are not fully heat treated. Plates 20a and 20b and magnet 16 are dimensioned such that air gap, 22, is formed at end, 24, of sensor 10 opposing wear surface 12. It should be mentioned that magnet portion 21 of sensor 10 may be embedded in brass, aluminum or fiberglass, as examples, to provide structural rigidity and protection from the elements (not shown in FIG. 1). Such materials may also provide isolation of sensor 10 from magnetically permeable materials from which wear part 14 may be fabricated.

Hall Effect probe, 26, or another magnetic flux measuring device, monitors the magnetic field in the air gap formed by the plates. Temperature sensor, 28, may be disposed in the vicinity of Hall probe 26 for measuring the temperature in gap 22 in order to correct magnetic flux measurements made by the Hall Effect probe for variations in temperature. Instrument package, 30, includes apparatus for controlling and transmitting the measurements from Hall probe 26 and temperature sensor 28 to a user-based receiver (not shown in FIG. 1). Instrument package 30 may be mounted on object or part 14.

FIG. 2A is a schematic representation of a side view of magnetic portion 21 of magnetic sensor 10 shown in FIG. 1 hereof, illustrating elongated permanent magnet 16 having at least two parallel sides, 31a, and 31b, and magnetic poles which are oriented perpendicularly to the sides 31a and 31b of magnet 16. The magnet is interposed between magnetically permeable plates 20a and 20b, and magnetic flux passes through plates 20a and 20b, and through air gap 22 (32a and 32b, and 32c, respectively).

Figure 2B:
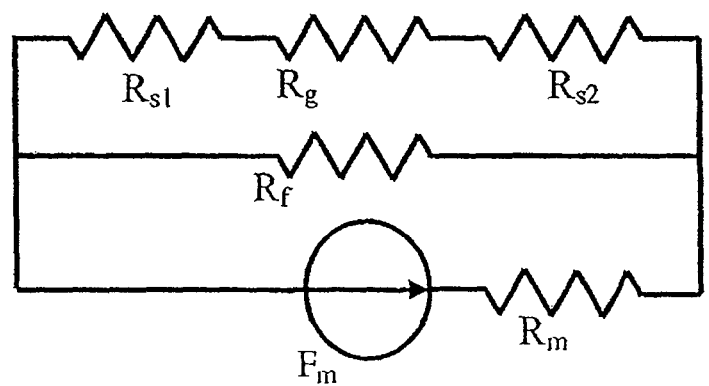
FIG. 2B is a magnetic circuit diagram for the magnetic portion shown in FIG. 2A.

FIG. 2B is a magnetic circuit diagram for the magnetic sensor shown in FIG. 2A, where the magnetic poles are perpendicular to the pole pieces, illustrating the relationship among the reluctances for gap 22, permanent magnet (PM) 16, pole pieces 20a and 20b, and fringe areas 32c and 32d. Here, $\phi_m$ represents the magnetic flux potential of magnet 16. Using reluctance circuit analysis for the magnetic circuit of FIG. 2B, one may obtain an analytical expression for the magnetic field $B_{gap}$ as follows:

$$B_{gap} = \frac{K_g H_c L_m (R_f + R_g + R_{s1} + R_{s2})}{A_g ((R_m R_f (R_m + R_f))(R_g + R_{s1} + R_{s2}))},$$

where $A_g$ is the area of air gap 22, $K_g$ is the air gap flux leakage factor, $H_c$ is the maximum coercive force, $L_m$ is the length of magnet 16 in the magnetization direction (direction of the magnetic flux vectors which are oriented in the direction from the magnetic south pole toward the north pole), and $R_f$ is the reluctance across the sides and ends of the magnetic portion of the sensor where fringing occurs, $R_g$ is the reluctance across the air gap where the magnetic field intensity is measured, $R_{s1}$ is the reluctance across magnetically permeable plate 20a, and $R_{s2}$ is the reluctance across second magnetically permeable plate 20b. Using reluctances $R_{s1}$ and $R_{s2}$ in the expression for $B_{gap}$ permits the situation where a pole piece and the magnet are not in actual or close contact, but rather as much as 0.25 in. apart. In such situations the measured reluctance includes that of the air gap formed between the magnet and the permeable plates.

The addition of the fringe reluctance allows a more accurate prediction of the flux in the gap, and gives some insight into the sensor design. By minimizing the air gap the fringing flux may be decreased, thereby decreasing the ratio of the fringing flux to the magnetic flux crossing the air gap. This increases the flux density in the air gap and improves the signal strength. Designing the sensor elements with a squarer aspect ratio will also decrease the ratio of the fringing flux to the flux crossing the air gap, although this effect is much smaller than that achieved by reducing dimensions of the air gap.

In the equation for $B_{gap}$, the reluctance factor $R_f$ is inversely proportional to the length of the magnet along the long axis of the sensor, while $R_{s1}$ and $R_{s2}$ are directly proportional to the length of the magnet along the long axis of the magnetic portion of the sensor, and $R_g$ is a constant. The resulting function of the magnet length versus magnetic flux density can be closely approximated by a $2^{nd}$-order polynomial for wear over more than 60% of the magnet length. The function becomes non-linear as the wear approaches 100% of the length of the magnet since $R_f$ requires division by zero as the magnet length approaches zero.

Figure 3A:
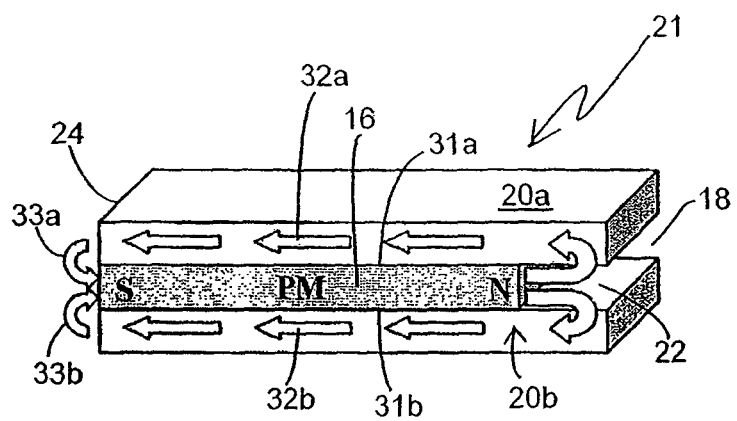

FIG. 3A is a schematic representation of a perspective view of magnetic portion 21 of sensor 10 shown in FIG. 1 hereof, showing the magnetic flux generated by an elongated permanent magnet having at least two parallel side, to which sides the magnetic poles are parallel. Magnetic flux 32a and 32b passes through magnetically permeable plates 20a and 20b, respectively, between which magnet 16 is interposed, and through air gap 22 formed plates 20a and 20b. Only one plate may be used in the parallel magnetic pole situation, in which case the magnet need only have one flat side.

Figure 3B:
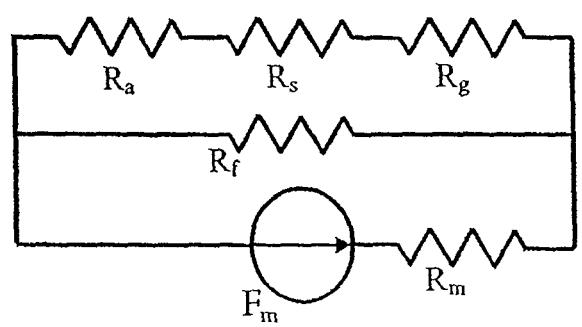
FIG. 3B is a magnetic circuit diagram for the magnetic portion shown in FIG. 3A applicable to the situation where only one magnetically permeable plate is employed.

Using reluctance circuit analysis solely for the top portion of the apparatus shown in FIG. 3A and the magnetic circuit shown in FIG. 3B, one may obtain an analytical expression for the magnetic field $B_{gap}$ as follows:

$$B_{gap} = \frac{K_g H_c L_m (R_f + R_g + R_s + R_a)}{A_g(R_m R_f + (R_m + R_f)(R_g + R_s + R_a))},$$

where $R_s$ is the reluctance across single magnetically permeable plate 20a shown in FIGS. 3B and $R_a$ is the reluctance, 33a, and 33b, through air across the magnet/plate interface at exposed magnet pole 24. The definitions of $R_f$ and $R_g$ are provided hereinabove.

Figure 4A:
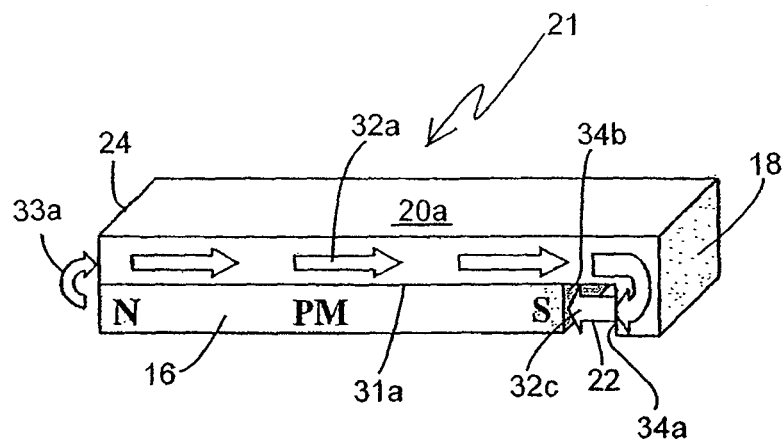
Figure 4B:
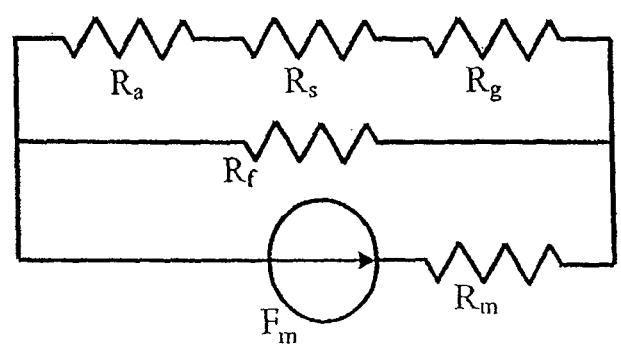
FIG. 4B is a magnetic circuit diagram for the magnetic portion of the magnetic sensor shown in FIG. 4A.

FIG. 4A is a schematic representation of a perspective view of the magnetic portion of the magnetic sensor shown in FIG. 1 hereof, showing the magnetic flux generated by elongated permanent magnet 16 having at least one flat side 31a and magnetic poles parallel to the flat side thereof. Magnetic flux 32a from magnet 16 passes through L-shaped plate 20a and magnetic flux, 32c, passes through air gap 22 formed between the short side, 34a, of L-shaped, magnetically permeable plate 20a and exposed end, 34b, of magnet 16 which is placed against the long side of the "L" and inside thereof. Gap 22 is located away from the portion 24 of the magnetic sensor exposed to wear. FIG. 4B is a magnetic circuit diagram for the portion of magnetic sensor 10 shown in FIG. 4A. An identical expression for $B_{gap}$ to that for FIG. 3B is obtained by using magnetic reluctance analysis of the magnetic circuit shown in FIG. 4B, except that $R_a$, the reluctance through air across the magnet/plate interface at exposed magnet pole 24, is now single component 33.

Figure 5A:
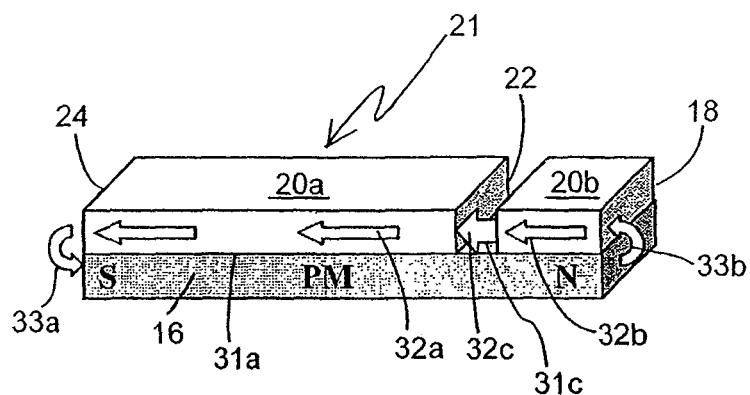

FIG. 5A is a schematic representation of a perspective view of the magnetic portion of magnetic sensor 10 shown in FIG. 1 hereof, showing the magnetic flux generated by elongated permanent magnet 16 having magnetic poles parallel to flat side 31a thereof, and passing principally through an air gap 22 formed by two spaced-apart magnetically permeable plates 20a and 20b disposed on flat side 31a of magnet 16, exposing portion, 31c, thereof.

Figure 5B:
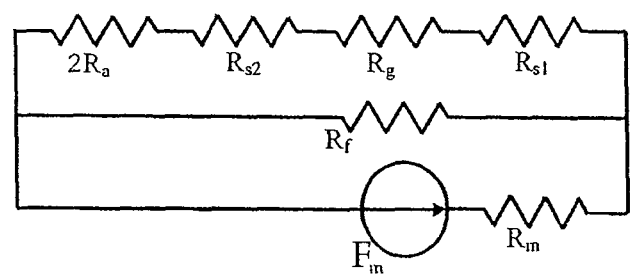
FIG. 5B is a magnetic circuit diagram for the magnetic portion shown in FIG. 5A.

Using reluctance circuit analysis for magnetic portion of sensor 10 shown in FIG. 5A and the magnetic circuit shown in FIG. 5B, one may obtain an analytical expression for the magnetic field $B_{gap}$ as follows:

$$B_{gap} = \frac{K_g H_c L_m (R_f + R_g + R_{s1} + R_{s2} + 2R_a)}{A_g(R_m + R_f + (R_m + R_f)(R_g + R_{s1} + R_{s2} + 2R_a))},$$

where $R_{s1}$ is the reluctance of plate 20a, $R_{s2}$ is the reluctance of plate 20b and $R_a$ is the sum of reluctances, 33a, and 33b, through air across the magnet/plate interface at exposed magnet poles 24 and 18, respectively. The definitions of $R_f$ and $R_g$ are provided hereinabove.

Figure 6A:
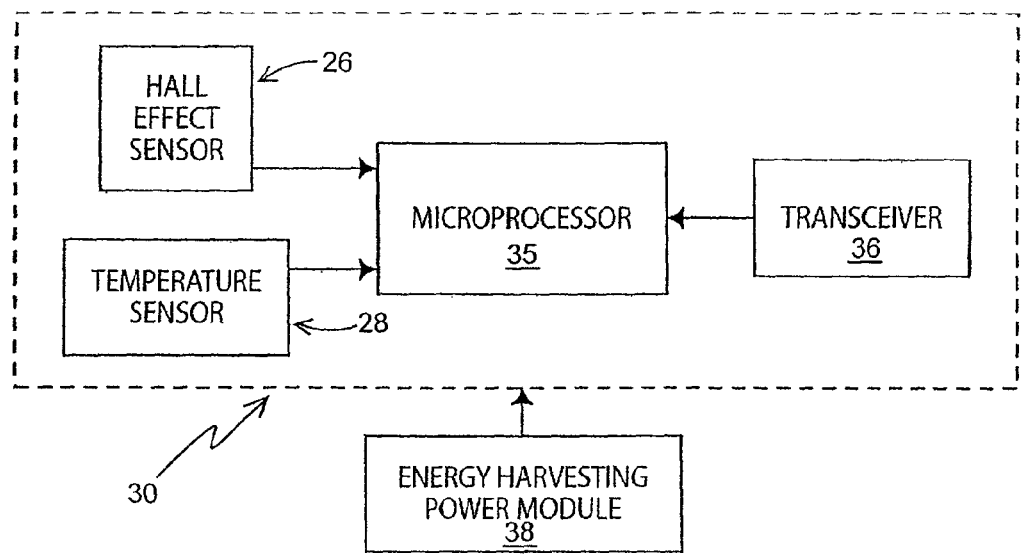

FIG. 6A is a schematic representation of an embodiment of instrument package 30 shown in FIG. 1 hereof. Measurements taken by Hall Effect sensor 26 and temperature sensor 28 are processed by microprocessor, 35, and information therefrom is directed to transceiver, 36, for transmittal to a user. Measurements from Hall Effect sensor 26 corrected by measurements from temperature sensor 28 may be used to calculate wear amounts and wear projections.

The user may be located remotely or may sample electronics package 30 using a reading device placed in the proximity of electronics package 30. A physical electronic link may also be employed. The present wear sensor 10 may be surrounded by a protective cover (not shown in FIG. 1), except for wear surfaces 12 and 18, to provide protection from harsh environments.

Electronics package 30 may be powered by batteries, rf energy generated by a reader brought close to package 30, or energy harvesting module, 38, as examples.

In many applications of present wear sensor 10, the operating environment makes a battery or a wired power supply for instrument package 30 associated with the sacrificial sensing element difficult, if not impossible. For snow plows, earth moving equipment, agricultural equipment, and the like, cold temperatures, severe vibrations, and/or contact or immersion in saline water may make the use of a replaceable battery, or even the inclusion of a charging connection for a sealed rechargeable battery, unfeasible. The locations of such sensors, often in inaccessible areas where blades and cutting edges contact road or soil surfaces, may also make the use of sealed inductive charging circuits impractical, and may increase the likelihood of damage to wired power.

To provide reliable power to the instrument package, energy may be harvested from the environmental vibrations that are inherent to the operation of these types of equipment. An embodiment of an energy harvesting system may include a transducer that converts vibrations to electrical energy, a storage device, and a control circuit to manage power flows. As examples, energy transducers may be piezoelectric, where mechanical strain energy may be converted into electrical voltage and current through piezoelectric materials or electroactive polymers, electrostatic, where pre-charged capacitor plates may be moved closer together and apart, mechanical, where the vibratory motions may be converted into rotary motion of an eccentric weight, or electromechanical, where a magnet may be moved relative to an electrical coil. Energy storage devices may include rechargeable batteries, or a low-leakage-loss capacitor. Commercially available control circuits and ICs are available for controlling the energy harvesting functions and may be provided by power management circuit, 44.

Figure 6B:
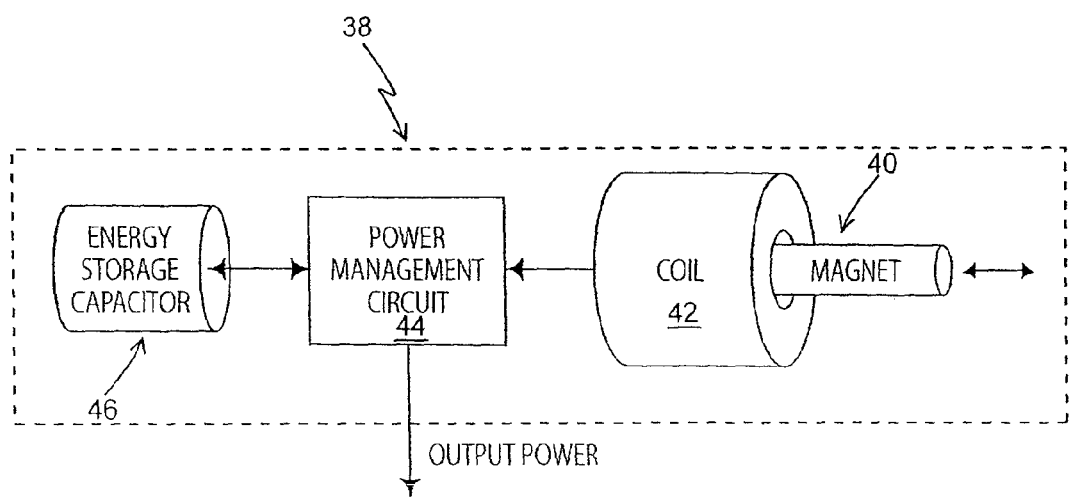
FIG. 6B is a schematic representation of an embodiment of the energy harvesting module shown in FIG. 6A hereof which derives electrical energy from a magnet and an electrical coil.

FIG. 6B is a schematic representation of an embodiment of energy harvesting module 38 shown in FIG. 3A hereof which derives electrical energy from magnet, 40, and electrical coil, 42. Magnet 40 moving relative to electrical coil 42 in cooperation with power management circuit 44 which may rectify the electrical signal therefrom, and storage capacitor, 46, is expected to be effective for powering electronics package 30, because an external induction coil (not shown in FIG. 3B) may be used at the time of installation of a new sacrificial sensing element 10 to activate instrument package 30 through coil 42 for obtaining initial readings and calibrating the element. Capacitors are useful as storage devices since they may be cycled millions of times, they are more resistant to vibration and shock damage than batteries, and their rates of charging and energy delivery are greater than batteries. Capacitors are generally heavier and bulkier than batteries having similar energy storage density, but such issues may not be important for many applications.

As an example of the operation of the combination of magnet 40 and electrical coil 42, for power generation, the operating environment of a snow plow may be considered. It is expected that an operating snow plow generates significant vibration between 1 and 20 Hz. Much of this vibration is directed along a vertical axis. Moreover, the plow will bounce when it is lifted from or lowered onto the road. Therefore, if magnet 40 is suspended in the vertical direction, in the vertically oriented bore of electrical coil 42, magnet 40 will oscillate therein, thereby inducing electrical voltage and current in the coil useful for charging capacitor 46.

Energy harvesting power module 38 for wear sensor 10 may rely on environmental vibration to charge capacitor 46 through control circuit 44. When a threshold voltage consistent with the power requirements of microprocessor 34, Hall Effect sensor 26, temperature sensor 28, and radio transceiver 36, is reached, power management circuit 44 switches power to instrument package 30 electrical systems, a measurement of the sacrificial wear element length is made by microprocessor 34 using magnetic field measurements from Hall Effect sensor 26, the value of the magnetic field measurement being adjusted for temperature using input from temperature sensor 28, and the adjusted value is transmitted to a user interface by wireless transceiver 36 using either a standard or proprietary network protocol having package collision detection and avoidance procedures such as random time delays or sequential sensor retention interrogation by the user interface. Energy harvesting system 38 may be sized to provide wear measurements having frequency sufficient to track the wear of the particular part or object being monitored. For the majority of applications half-hour to hourly measurements are expected to resolve the wear to increments of less than 1%.

Figure 7:
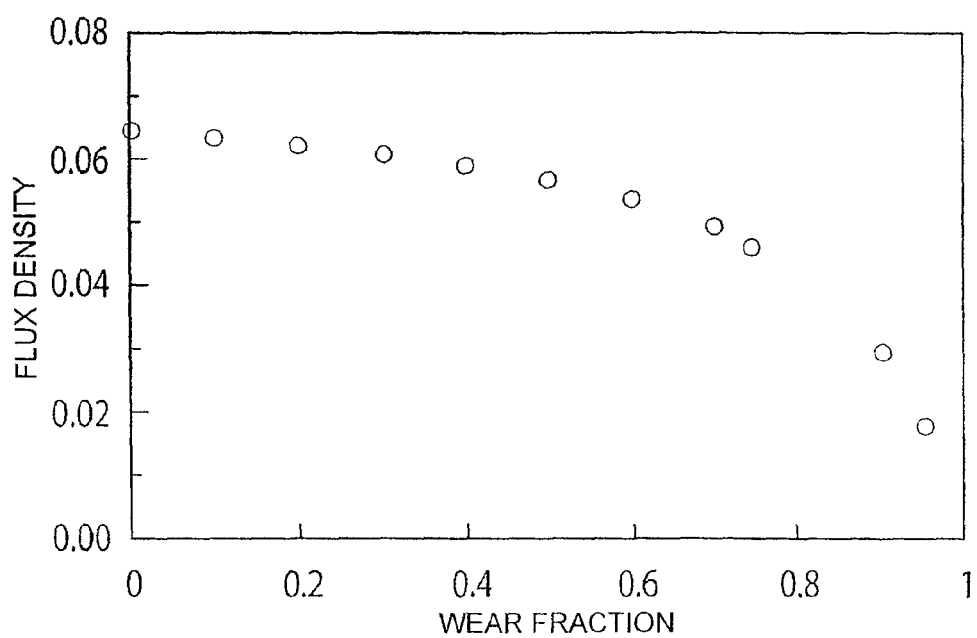
FIG. 7 is a graph of the calculated flux density in the gap as a function of wear fraction of the magnet and the surrounding pole pieces.

FIG. 7 is a graph of the calculated flux density in the gap as a function of wear fraction of the magnet and the surrounding pole pieces.

Having generally described certain embodiments of the invention, the following EXAMPLE provides additional details:

EXAMPLE

Elongated permanent magnet 16 may have dimensions: 2.0" in length, 0.5" in width, and 0.125" in thickness, and permeable plates 20a and 20b may have dimensions: 2.25" in length, 0.5" in width, and 0.125" in thickness. The gap thickness may be 0.125" and the gap area 0.125 in.$^2$. Assuming a magnet having perpendicular poles and a residual flux density of 1600 Gauss, the steel being 1018 steel, and having a relative permeability of 1000, the gap fringe factor, $K_f$, is estimated to be 0.8, and the maximum gap flux density, $B_{gap}$ is 0.064 Tesla for the unworn magnetic sensor 10. $B_{gap}$ declines to 0.41 Tesla as permanent magnet 16 within sensor 10 is worn to 0.75" in length. Typical reluctance values for $R_m$, $R_f$, $R_s$, and $R_g$ may be $3.57 \times 10^6$ H$^{-1}$, $6.60 \times 10^6$ H$^{-1}$, $5.64 \times 10^5$ H$^{-1}$, and $3.13 \times 10^7$, respectively, for an unworn magnetic sensor 10, and $8.94 \times 10^6$ H$^{-1}$, $1.27 \times 10^7$ H$^{-1}$, $2.82 \times 10^5$ H$^{-1}$, and $3.13 \times 10^7$ H$^{-1}$, respectively, when magnet 16 of magnetic sensor 10 is worn to 0.75" in length. The fringing area and the magnet area both decrease as the magnet is worn. Since reluctance is equal to the length of the flux path divided by the permeability, and multiplied by the cross sectional area, as the area decreases, the reluctance will increase.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A wear sensor comprising in combination:
    an elongated magnet having a first length along a long dimension thereof, a first long flat side and an opposing second, long flat side;
    a first magnetically permeable material having a second length and a flat side disposed alongside the first long flat side of said magnet;
    a second magnetically permeable material having a third length and a flat side disposed alongside the second long flat side of said magnet, wherein the second length and the third length are greater than the first length, forming thereby a closed end and an air gap between said first magnetically permeable material and said second magnetically permeable material at the opposing end; and
    means for measuring the magnetic field within the air gap;
    whereby the magnetic field in the air gap decreases as said magnet, said first material and said second material are worn away at the closed end.

2. The apparatus of claim 1, wherein the second length and the third length are equal.

3. The apparatus of claim 1, wherein said means for measuring magnetic field comprises a Hall Effect probe.

4. The apparatus of claim 3, further comprising a temperature sensor for correcting for temperature variations in the measured magnetic field by said Hall Effect probe.

5. The apparatus of claim 1, wherein the first long flat side of said magnet is parallel to the second long flat side thereof.

6. The apparatus of claim 1, wherein said magnet has a pole direction perpendicular to the first flat side and the second flat side thereof.

7. The apparatus of claim 1, wherein said magnet has a pole direction parallel to the first flat side and the second flat side thereof.

8. The apparatus of claim 1, wherein the flat side of said first magnetically permeable material is adjacent to the first side of said magnet, and wherein the flat side of said second magnetically permeable material is adjacent to the second flat side of said magnet.

9. The apparatus of claim 1, wherein said magnet comprises flexible magnet material.

10. The apparatus of claim 1, wherein said magnet comprises a rectangular magnet, wherein said first magnetically permeable material comprises a rectangular plate, and said second magnetically permeable material comprises a rectangular plate.

11. A method for determining wear experienced by an object, comprising the steps of:
    interposing an elongated magnet having a first length along a long dimension thereof, a first long flat side and an opposing second long flat side between a first magnetically permeable material having a second length and a flat side disposed alongside the first long flat side of the magnet, and a second magnetically permeable material having a third length and a flat side disposed alongside the second long flat side of the magnet, wherein the second length and the third length are greater than the first length, forming thereby a closed end and an air gap between the first magnetically permeable material the second magnetically permeable material at the opposing end;

exposing the closed end to the same wear as experienced by the object; and measuring the magnetic field within the air gap;

whereby the magnetic field in the air gap decreases as the magnet, the first material and the second material are worn away at the closed end.

12. The method of claim 11, wherein the second length and the third length are equal.

13. The method of claim 11, wherein the means for measuring magnetic field comprises a Hall Effect probe.

14. The method of claim 13, further comprising a temperature sensor for correcting for temperature variations in the measured magnetic field by the Hall Effect probe.

15. The method of claim 11, wherein the first flat side of the magnet is parallel to the second flat side thereof.

16. The method of claim 11, wherein the magnet has a pole direction perpendicular to the first long flat side and the second long flat side thereof.

17. The method of claim 11, wherein the magnet has a pole direction parallel to the first long flat side and the second long flat side thereof.

18. The method of claim 11, wherein the flat side of the first magnetically permeable material is adjacent to the first side of the magnet, and wherein the flat side of the second magnetically permeable material is adjacent to the second flat side of said magnet.

19. The method of claim 11, wherein the magnet comprises flexible magnet material.

20. The method of claim 11, wherein the magnet comprises a rectangular magnet, wherein the first magnetically permeable material comprises a rectangular plate, and the second magnetically permeable material comprises a rectangular plate.

21. A wear sensor comprising in combination:

an elongated magnet having a first length along a long dimension thereof, a long flat side, and a pole direction parallel to the flat side;

a first magnetically permeable material having a second length and a flat side disposed alongside the flat side of said magnet;

a second magnetically permeable material having a third length and a flat side disposed alongside the long flat side of said magnet, wherein the second length and the third length are less than the first length, wherein said magnet and said first magnetically permeable material form a first closed end, wherein said magnet and said second magnetically permeable material form an opposing second closed end, and wherein said first magnetically permeable material and said second magnetically permeable material form an air gap therebetween on the flat side of said magnet; and means for measuring the magnetic field within the air gap;

whereby the magnetic field in the air gap decreases as said magnet, and said first magnetically permeable material are worn away at the first closed end.

22. The apparatus of claim 21, wherein said means for measuring magnetic field comprises a Hall Effect probe.

23. The apparatus of claim 22, further comprising a temperature sensor for correcting for temperature variations in the measured magnetic field by said Hall Effect probe.

24. The apparatus of claim 21, wherein the flat side of said first magnetically permeable material is adjacent to the long flat side of said magnet, and wherein the flat side of said second magnetically permeable material is adjacent to the long flat side of said magnet.

25. The apparatus of claim 21, wherein said magnet comprises flexible magnet material.

26. The apparatus of claim 21, wherein said magnet comprises a rectangular magnet, wherein said first magnetically permeable material comprises a rectangular plate, and said second magnetically permeable material comprises a rectangular plate.

27. A wear sensor comprising in combination:

an elongated magnet having a first length along a long dimension thereof, a long flat side, and a pole direction parallel to the first flat side;

a magnetically permeable material having a second length and a flat side disposed alongside the long flat side of said magnet, wherein the second length is greater than the first length, forming thereby a closed end and an opposing end wherein said magnetically permeable material extends beyond the flat side of said elongated magnet; and means for measuring the magnetic field in the vicinity of the extended magnetically permeable material;

whereby the magnetic field in vicinity of the extended magnetically permeable material decreases as said magnet and said magnetically permeable material are worn away at the closed end.

28. The wear sensor of claim 27, wherein said extended permeable material is 'L'- shaped with the long side of the 'L' disposed alongside the flat side of said magnet, whereby an air gap is formed between the short section of said 'L' shaped material and said elongated magnet at the opposing end from the closed end thereof, wherein the magnetic field is measured in the air gap by said means for measuring the magnetic field.

29. The apparatus of claim 27, wherein said means for measuring magnetic field comprises a Hall Effect probe.

30. The apparatus of claim 29, further comprising a temperature sensor for correcting for temperature variations in the measured magnetic field by said Hall Effect probe.

31. The apparatus of claim 27, wherein the flat side of said magnetically permeable material is adjacent to the long flat side of said magnet.

32. The apparatus of claim 27, wherein said magnet comprises flexible magnet material.

33. The apparatus of claim 27, wherein said magnet comprises a rectangular magnet, and wherein said magnetically permeable material comprises a rectangular plate.

* * * * *